(12) United States Patent
Phan et al.

(10) Patent No.: US 6,572,372 B1
(45) Date of Patent: Jun. 3, 2003

(54) EMBEDDED FEATURES AND METHODS OF A DENTAL APPLIANCE

(75) Inventors: Loc X. Phan, Milpitas, CA (US); Muhammad Chishti, Sunnyvale, CA (US); Ross J. Miller, Sunnyvale, CA (US); H. Robert Van Den Berg, San Ramon, CA (US); Eric Kuo, San Francisco, CA (US); Jae Hyun Ahn, San Francisco, CA (US)

(73) Assignee: Align Technology, Inc., Santa Clara, CA (US)

( * ) Notice: Subject to any disclaimer, the term of this patent is extended or adjusted under 35 U.S.C. 154(b) by 0 days.

(21) Appl. No.: 09/616,222

(22) Filed: Jul. 14, 2000

Related U.S. Application Data

(60) Provisional application No. 60/199,649, filed on Apr. 25, 2000, and provisional application No. 60/199,650, filed on Apr. 25, 2000.

(51) Int. Cl.[7] ................................................ A61C 7/00
(52) U.S. Cl. ............................................. 433/6; 433/18
(58) Field of Search ................................ 433/6, 18, 20, 433/24, 215; 128/861

(56) References Cited

U.S. PATENT DOCUMENTS

| | | |
|---|---|---|
| 3,407,500 A | 10/1968 | Kesling |
| 3,600,808 A | 8/1971 | Reeve |
| 3,660,900 A | 5/1972 | Andrews |
| 3,682,502 A | 8/1972 | Wallshein |
| 3,860,803 A | 1/1975 | Levine |
| 3,922,786 A | 12/1975 | Lavin |
| 3,950,851 A | 4/1976 | Bergersen |
| 4,150,485 A | 4/1979 | Lee, Jr. et al. ............ 523/115 |
| 4,253,828 A | 3/1981 | Coles et al. |
| 4,324,546 A | 4/1982 | Heitlinger et al. |
| 4,324,547 A | 4/1982 | Arcan et al. |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,591,341 A | 5/1986 | Andrews |
| 4,609,349 A | 9/1986 | Cain |

(List continued on next page.)

FOREIGN PATENT DOCUMENTS

| | | |
|---|---|---|
| FR | 2369828 | 6/1978 |
| WO | WO 94/10935 | 5/1994 |
| WO | WO 98/32394 | 7/1998 |
| WO | WO 98/58596 | 12/1998 |

OTHER PUBLICATIONS

Andrews, "The Six Keys to Optimal Occlusion" *Straight Wire*, Chapter 3 pp13–24.

(List continued on next page.)

*Primary Examiner*—Kevin Shaver
*Assistant Examiner*—Melba Bumgarner
(74) *Attorney, Agent, or Firm*—Townsend and Townsend and Crew LLP; Lynn M. Thompson

(57) ABSTRACT

Traditional orthodontic treatment often involves the use of basic repositioning devices, such as braces, and the use of supplementary devices, components or accessories to achieve desired end results. Such components may be mounted on fixed, non-removable devices or they may be part of a removable appliance typically worn prior to the application of the fixed devices. As with traditional treatment, it may be desired to utilize similar components when repositioning teeth with removable elastic repositioning appliances. Due to the nature of elastic appliances, such components may take a variety of forms ranging from readily available traditional accessories to specially created devices. Thus, traditional components may be mounted on or embedded in an elastic appliance, or the appliance may be formed to provide similar components. Likewise, the appliance may be modified to provide additional features for specific orthodontic treatments.

1 Claim, 14 Drawing Sheets

U.S. PATENT DOCUMENTS

| | | | |
|---|---|---|---|
| 4,664,626 A | | 5/1987 | Kesling |
| 4,676,747 A | | 6/1987 | Kesling |
| 4,755,139 A | | 7/1988 | Abbatte et al. |
| 4,793,803 A | | 12/1988 | Martz |
| 4,798,534 A | | 1/1989 | Breads |
| 4,836,778 A | | 6/1989 | Baumrind et al. |
| 4,837,732 A | | 6/1989 | Brandestini et al. |
| 4,850,865 A | | 7/1989 | Napolitano |
| 4,856,991 A | | 8/1989 | Breads et al. |
| 4,877,398 A | | 10/1989 | Kesling |
| 4,880,380 A | | 11/1989 | Martz |
| 4,936,862 A | | 6/1990 | Walker et al. |
| 4,941,826 A | | 7/1990 | Loran et al. |
| 4,983,334 A | | 1/1991 | Adell |
| 5,011,405 A | | 4/1991 | Lemchen |
| 5,017,133 A | | 5/1991 | Miura |
| 5,022,855 A | | 6/1991 | Jeckel ........................ 433/18 |
| 5,035,613 A | | 7/1991 | Breads et al. |
| 5,055,039 A | | 10/1991 | Abatte et al. |
| 5,059,118 A | | 10/1991 | Breads et al. |
| 5,100,316 A | | 3/1992 | Wildman |
| 5,125,832 A | | 6/1992 | Kesling |
| 5,139,419 A | | 8/1992 | Andreiko et al. |
| 5,145,364 A | | 9/1992 | Martz et al. |
| 5,186,623 A | | 2/1993 | Breads et al. |
| 5,273,429 A | | 12/1993 | Rekow et al. |
| 5,338,198 A | | 8/1994 | Wu et al. |
| 5,340,309 A | | 8/1994 | Robertson |
| 5,342,202 A | | 8/1994 | Deshayes |
| 5,367,478 A | | 11/1994 | Hattori |
| 5,368,478 A | | 11/1994 | Andreiko et al. |
| 5,382,164 A | | 1/1995 | Stern |
| 5,395,238 A | | 3/1995 | Andreiko et al. |
| 5,431,562 A | | 7/1995 | Andreiko et al. |
| 5,447,432 A | | 9/1995 | Andreiko et al. |
| 5,452,219 A | | 9/1995 | Dehoff et al. |
| 5,454,717 A | | 10/1995 | Andreiko et al. |
| 5,456,600 A | | 10/1995 | Andreiko et al. |
| 5,474,448 A | | 12/1995 | Andreiko et al. |
| 5,528,735 A | | 6/1996 | Strasnick et al. |
| 5,533,895 A | | 7/1996 | Andreiko et al. |
| 5,536,169 A | * | 7/1996 | Yousefian ...................... 433/6 |
| 5,542,842 A | | 8/1996 | Andreiko et al. |
| 5,549,476 A | | 8/1996 | Stern |
| 5,587,912 A | | 12/1996 | Anderson et al. |
| 5,605,459 A | | 2/1997 | Kuroda et al. |
| 5,607,300 A | | 3/1997 | Tepper ........................... 433/6 |
| 5,607,305 A | | 3/1997 | Andersson et al. |
| 5,645,420 A | | 7/1997 | Bergersen |
| 5,645,421 A | | 7/1997 | Slootsky |
| 5,683,243 A | | 11/1997 | Andreiko et al. |
| 5,683,244 A | * | 11/1997 | Truax ............................ 433/6 |
| 5,692,894 A | | 12/1997 | Schwartz et al. |
| 5,725,376 A | | 3/1998 | Poirier |
| 5,725,378 A | | 3/1998 | Wang |
| 5,800,174 A | | 9/1998 | Andersson |
| 5,866,058 A | | 2/1999 | Batchelder et al. |
| 5,879,158 A | | 3/1999 | Doyle et al. |
| 5,880,961 A | | 3/1999 | Crump |
| 5,951,291 A | | 9/1999 | Albert et al. ................. 433/21 |
| 5,957,686 A | | 9/1999 | Anthony |
| 5,964,587 A | | 10/1999 | Sato |
| 5,971,754 A | | 10/1999 | Sondhi et al. |
| 5,975,893 A | | 11/1999 | Chishti et al. ................. 433/6 |
| 6,044,309 A | | 3/2000 | Honda |
| 6,049,743 A | | 4/2000 | Baba |
| 6,123,544 A | | 9/2000 | Cleary |
| 6,183,248 B1 | | 2/2001 | Chishti et al. |
| 6,190,165 B1 | | 2/2001 | Andreiko et al. |
| 6,217,334 B1 | | 4/2001 | Hultgren |

OTHER PUBLICATIONS

Biostar Opeation & Training Manual. Great Lakes Orthodontics, Ltd. 199 Fire Tower Drive, Tonawanda, New York. 14150–5890. 20 pages total.

Chiappone, "Constructing the gnathologic setup and positioner" *J. Clin. Orthod.* (1980) 14:121–133.

Cottingham, "Gnathologic clear plastic positioner" *Am. J. Orthod.* (1969) 55:23–31.

Cureton, "Correcting malaligned mandibular incisors with removable retainers" *J. Clin. Orthod.* (1996) 30:390–395.

Dent–X posted at http://www.dent–x.com/DentSim.htm Sep. 24, 1998, 6 pages total.

Elsasser, "Some observations on the history and uses of the Kesling positioner" *Am. J. Orthod.* (1950) 36:368–374.

Kamada et al., "Case reports on tooth positioners using LTV vinyl silicone rubber" *J. Nihon University School of Dentistry* (1984) 26(1):11–29.

Kamada et al., "Construction of tooth positioners with LTV vinyl silicone rubber and some case reports" *J. Nihon University School of Dentistry* (1982) 24(1):1–27.

Kesling, "Coordinating the predetermined pattern and tooth positioner with conventional treatment" *Am. J. Orthod. Oral. Surg.* (1946) 32:285–293.

Kesling, "The philosophy of the tooth positioning appliance" *Am. J. Orthod. Oral. Surg.* (1945) 31(6):297–304.

Kleeman et al., "The speed positioner" *J. Clin. Orthod.* (1996) 30:673–680.

Kunii et al., "Articulation Simulation for an Intelligent Dental Care System" *Displays* (1994) 15:181–188.

Kuroda et al., "Three–dimensional dental cast analyzing system using laser scanning" *Am. J. Orthod. Dentofac. Orthop.* (1996) 110:365–369.

Nahoum et al., "The vacuum formed dental contour appliance" *The New York State Dental Journal* (1964) 30(9):385–390.

*Nippon Dental Review* "New orthodontic device–dynamic positioner (D.P.)–I. Approach to the proposal of D.P. and transparent silicone rubber" (1980) 452:61–74.

*Nippon Dental Review,* "New orthodontic device–dynamic positioner (D.P.)–II. Practical application and construction of D.P." (1980) 454:107–130.

*Nippon Dental Review* "New orthodontic device–dynamic positioner (D.P.)–III. Case reports of reversed occlusion" 1980) 457:146–164.

*Nippon Dental Review* "New orthodontic device–dynamic positioner (D.P.)–Case reports of reversed occlusion" (1980) 458:112–129.

Nishiyama et al., "A new construction of tooth repositioner by LTV vinyl silicone rubber" *J. Nihon University School of Dentistry* (1977) 19(2):93–102.

Cardinal Industrial Finishes, Powder Coatings information posted at http://www.cardinalpaint.com on Aug. 25, 2000, 2 pages total.

Proffit et al, "Contemporary Orthodontics" Second Edition, Chapter 15, pp 470–533.

*Raintree Essix™ & ARS Materials, Inc.,* Raintree Essix™ Technical Magazine Table of Contents and Essix™ Applications, http://www.essix.com/magazine/default.html (Aug. 13, 1997) 7 pages total.

Richmond et al., "The development of the PAR Index (Peer Assessment Rating): reliability and validity" *European Journal of Orthodontics* (1992) 14:125–139.

Schroeder et al., Eds. *The Visual Toolkit*, Prentice Hall PTR, New Jersey (1998) Chapters 6, 8, and 9 (pp. 153–210, 309–354, and 355–428, respectively).

Shilliday, "Minimizing finishing problems with the mini–positioner" *Am. J. Orthod.* (1971) 59:596–599.

Warunek et al., "Clinical use of silicone elastomer appliances" *JCO* (1989) XXIII(10):694–700.

Warunek et al., "Physical and mechanical properties of elastomers in orthodontic positioners" *Am. J. Orthod. Dentofac. Orthop.* (1989) 95:388–400.

Wells, "Application of the positioner appliance in orthodontic treatment" *Am. J. Orthodont.* (1970) 58:351–366.

* cited by examiner

EMBEDDED FEATURES AND METHODS OF A DENTAL APPLIANCE

CROSS-REFERENCES TO RELATED APPLICATIONS

This Application claims the benefits of prior provisional application Nos. 60/199,649 and 60/199,650, both filed on Apr. 25, 2000, the full disclosures of which are incorporated herein by reference. The disclosure of this application is related to copending application Ser. No. 09/616,830, filed on the same day, the full disclosure of which is incorporated herein by reference.

BACKGROUND OF THE INVENTION

The present invention is related generally to the field of orthodontics. Particularly, this invention relates to the use of removable orthodontic appliances for producing tooth movements. More particularly, this invention relates to improved devices, systems and methods for producing such tooth movements with elastic repositioning appliances.

Orthodontic treatments involve repositioning misaligned teeth and bite configurations for improved cosmetic appearance and dental function. Repositioning teeth is accomplished by applying controlled forces to the teeth over an extended period of time. This is conventionally accomplished by wearing what are commonly referred to as "braces." Braces are typically comprised of brackets or bands which are bonded to the teeth and linked with the use of archwires, ligatures and O-rings. After the archwire is in place, periodic appointments with the orthodontist are required, during which the patient's braces will be adjusted. This involves installing different archwires having different force-inducing properties or by replacing or tightening existing ligatures. Between meetings, the patient may be required to wear supplementary appliances, such as elastic bands or headgear, to supply additional or extraoral forces.

Although conventional braces are effective, they are often a tedious and time consuming process requiring many visits to the orthodontists office. Moreover, from a patient's perspective, they are unsightly and uncomfortable. The archwire and ligatures which connect the brackets in a continuous network make brushing, flossing between the teeth and other dental hygiene procedures difficult, possibly contributing to the development of gingivitis, caries, and other dental disease. Consequently, alternative orthodontic treatments are needed. In particular, it would be desirable to use appliances which can be removed by the patient during daily dental hygiene routines, while participating in athletic activities, or for cosmetic purposes.

A particularly promising approach relies on the use of elastic positioning appliances for realigning teeth. Such appliances comprise a thin shell of elastic material that generally conforms to a patient's teeth but is slightly out of alignment with the initial tooth configuration. Placement of the elastic positioner over the teeth applies controlled forces in specific locations to gradually move the teeth into the new configuration. Repetition of this process with successive appliances comprising new configurations eventually move the teeth through a series of intermediate configurations to a final desired configuration. A full description of an exemplary elastic polymeric positioning appliance is described in U.S. Pat. No. 5,975,893, and in published PCT application WO 98/58596 which designates the United States and which is assigned to the assignee of the present invention. Both documents are incorporated by reference for all purposes.

In addition to their ease of use, polymeric positioning appliances are generally transparent, providing an improved cosmetic appearance, and impart substantial force on the teeth, due to stiffness of the appliance. The stiffness of an elastic positioning appliance is a result of the modulus of the thermoformable polymer materials from which it is made. The higher the modulus of the materials, the higher the stiffness of the appliance. By designing the appliance to cover the teeth, a much larger and/or more varied contact surface area may be afforded compared to traditional spring retainers and wire-based appliances. Consequently, more dramatic tooth movements may be achieved.

In some cases, however, orthodontic treatment may involve more complex tooth movements or treatment plans requiring additional devices or accessories. For example, it may be desirable to apply forces to surfaces of the teeth that may not be easily achieved by the appliance alone, either due to the location or characteristics of the surface itself or of the surrounding teeth. Similarly, it may be desirable to apply extraoral forces to some tooth surfaces to achieve certain tooth movements or to control growth and development of the bite and jaws. Likewise, it may be desirable to achieve such control indirectly through soft tissue stretch and muscular activity. Alternatively, it may be preferable to allow the passive eruption and movement of certain teeth, free of applied forces. The devices and accessories commonly utilized for these situations are typically separate removable appliances worn prior to the application of conventional braces, or accessories used in conjunction with conventional braces. Thus, such devices and accessories may not be compatible with the use of elastic polymeric positioning appliances for orthodontic treatment.

Consequently, improved methods and apparatus for achieving these treatment objectives are desired for complete orthodontic treatment in such patients. Such devices, systems and methods would maintain the advantages of and be compatible with a removable appliance while providing supplementary features to assist in the improvement of jaw structuring, alignment and tooth repositioning, to name a few. At least some of these objectives will be met by the designs and methods of the present invention described hereinafter.

SUMMARY OF THE INVENTION

The present invention provides improved devices, systems and methods for repositioning teeth from a first orientation to a successive orientation in a series of movements to a final tooth and bite configuration. Such repositioning is based on a system comprising at least one and usually a plurality of three or more elastic repositioning appliances configured to receive the teeth in a cavity and incrementally reposition individual teeth, usually in a series of successive steps. In cases involving more complex movements or treatment plans, it may be desired to utilize additional devices, components or accessories. The present invention provides for the utilization of such devices, components or accessories typically used in conventional orthodontic treatment. In some instances the present invention provides improved elastic repositioning appliances that take the place of such additional accessories. Further, the present invention may provide improved elastic repositioning appliances that provide simultaneous repositioning of tooth and bite configurations that may be unachievable with conventional devices.

In a first aspect of the present invention, a removable elastic positioning appliance, typically used in a series of successive elastic appliances for orthodontic treatment, may be comprised of a polymeric shell having at least one orthodontic component or accessory. These components or accessories may be independent entities that are embedded in the polymeric shell during production of the appliance. Or, they may be mounted on the polymeric shell with a suitable adhesive in a post-production assembly protocol. In either case, the components may be traditional accessories that are typically used with conventional orthodontic devices, such as braces, or they may be any other readily available components used for dental treatment. Alternatively, the components may be specially created accessories designed for specific purposes when used with removable elastic positioning appliances. Such specially created accessories may be independent entities present on or in the polymeric shell as described above, or they may be formed by the polymeric shell itself. In these cases, the component may be a formed protrusion or shape in the wall of the polymeric shell, providing a variety of advantages, including but not limited to increased stability, safety from breakage, ease of manufacturing, cost savings, shortened treatment time and improved cosmetic appearance and patient compliance.

In a first embodiment, the orthodontic components or accessories may be conventional accessories typically used with fixed, non-removable orthodontic devices. For example, headgear tubes are conventional accessories typically mounted on traditional braces for inserting a headgear device and applying extraoral force to the teeth and jaws. Tubes for receiving headgear may be mounted on or embedded in the polymeric shell of an elastic positioning appliance for a similar effect. Similarly, orthodontic hooks may be mounted on traditional braces to support elastic bands which may also apply distinct forces to the teeth and jaws. As with headgear tubes, such hooks may also be mounted on or embedded in the polymeric shell of a positioning appliance for a similar effect. Likewise, a number of other conventional accessories, such as brackets, springs, bumper tubes, palatal bars, frameworks, pin-and-tube apparatuses and the like, may be used in conjunction with polymeric positioning appliances. In some cases, such as with brackets, the accessory may be used to join a removable elastic appliance with a portion of teeth supporting fixed conventional devices, such as braces.

In a second embodiment, the orthodontic components or accessories may be those which are primarily exclusive to removable appliances. These components are not generally suited for use with fixed appliances and devices due to their bulk and size. In addition, they are often used prior to the use of fixed devices to create a favorable environment for later tooth repositioning. For example, when a patient's teeth are still erupting, a number of devices may be used to foster improved eruption and development of the tooth arrangement and bite configuration. These may include buccal shields, buccinator bows or wire shields, bite plates, palatal expanders and bars, lingual flanges and pads, lip pads or bumpers, and the like. Since these components are currently used with removable appliances, they are ideally suited for use with removable elastic positioning appliances. Thus, the components may be mounted on or embedded in the polymeric shell of an elastic appliance. Similarly supporting structures for such components may also be mounted or embedded in the polymeric shell for the removable application of a component. For example, a bumper tube may be embedded in the polymeric shell for later insertion and removal of a bumper. Alternatively, the components may be formed by the appliance itself, such components comprising a formed protrusion or shape in the wall of the polymeric shell. In these cases, the elastic repositioning appliance may take the place of any additional accessories.

An added advantage of the use of elastic repositioning appliances having these components or accessories is the ability to provide the conventional benefit of the accessory while simultaneously repositioning the teeth, a combination previously limited. In conventional treatment, the use of fixed devices to reposition the teeth negated the ability of simultaneously using accessories provided by some removable appliances since removable appliances may not be readily applied with fixed devices in place. For example, situations in which it is desired to control eruption of specific teeth concomitant with repositioning of the same or other teeth would cause great difficulty if not an impossible dilemma with traditional devices. The present invention may provide such simultaneous maneuvers which are unachievable with conventional treatment.

In a second aspect of the present invention, a removable dental positioning appliance, typically used in a series of successive elastic appliances for orthodontic treatment, may be comprised of at least one protrusion shaped to be used for an orthodontic function. As described above, such a protrusion may resemble, in form or function, a traditional component or accessory used in conventional orthodontic treatment with fixed, non-removable devices or with removable appliances. For example, an appliance may have a protrusion or shape in the wall of the polymeric shell in the form of a hook for mounting flexible bands, ligatures or adjunct devices. Such a hook may resemble traditional hooks found in dental care, or it may be specially designed for use with elastic repositioning appliances. Likewise, such a protrusion may form a spring which transmits force to one or more teeth to reposition teeth from a first arrangement to a successive arrangement. A spring of this type may be of a traditional design or it may be specially designed for use with elastic repositioning appliances. Further, it may be specially designed to engage an attachment body mounted on a tooth, a device primarily utilized in conjunction with removable elastic appliances. A full description of exemplary attachment bodies and devices is described in published PCT application WO 99/28228, which corresponds to co-pending application Ser. No. 09/454278, assigned to the assignee of the present invention. Both documents are incorporated by reference for all purposes. Thus, in these and similar cases, such as a palatal bar, the protrusion may take the place of a traditional accessory or component, or it may be utilized in a specialized manner.

In one embodiment, the protrusion may contact one or more dental surfaces to assist in holding the elastic appliance in position. For example, one or more protrusions may be sized and located to contact interdental areas of the patient's teeth, often near the gingival margin, when the appliance is properly inserted and positioned. Such protrusions may be formed in the wall of the polymeric shell, or they may be adhered to or embedded into the polymeric shell to protrude from the wall. Such placement of the protrusions may provide additional friction and "grab" in dental regions conducive to this effect. Similarly, a protrusion may be sized and located to contact a tooth along a portion of the gingival margin, with or without contact in the interdental areas. Or, the protrusion may be a continuous protrusion contacting more than one tooth along the gingival margin and the interdental areas. In each of these cases, the contact of the protrusion may assist in holding the appliance in proper position.

In another embodiment, the one or more protrusions may form a bite plate. A bite plate is a device which prevents the teeth from closing completely. By opening the bite in this manner, unopposed teeth may be allowed to passively erupt in a controlled manner to beneficially alter vertical dental relationships. In addition, such an open state or disclusion may relieve teeth which are in crossbite allowing orthodontic forces to correct the crossbite.

To provide anterior disclusion, an elastic positioning appliance may have an increase in thickness of material in the posterior occlusal regions. This increase in thickness may be applied to the appliance or formed by the appliance to create a protrusion over the designated occluding surfaces. Similarly, posterior disclusions may be provided by forming a protrusion which extends at least a portion of an upper palatal region with added thickness. Alternatively, posterior disclusions may be provided by forming a protrusion in an upper lingual or lower facial anterior region. Such protrusions may prevent the front teeth from closing completely, thus discluding the posterior teeth. As previously described, such protrusions may be formed in the appliance or applied to the surface of the appliance.

Such embodiments of the present invention may be utilized in the treatment of patients with a condition commonly termed a "deep bite". In these cases, the lower teeth contact the upper teeth and/or the palate in the natural bite. This occurs when the posterior teeth are not fully erupted in the correct position allowing the anterior teeth to become overdosed or overlap more than is desirable. Such a bite is injurious to the palate, tends to crowd the lower teeth, and affects flaring of the upper teeth leading to upper spaces. This may be alleviated with the use of a bite plate which provides posterior disclusion. Such disclusion allows the posterior teeth to naturally erupt without contacting the opposing teeth which may impede their eruption into the correct position. The present invention may provide the function of a bite plate while additionally providing repositioning forces and other orthodontic treatment to the patient. These functions may be simultaneous, an attribute not previously afforded by conventional orthodontic treatment.

In a third aspect of the present invention, a removable dental positioning appliance, typically used in a series of successive elastic appliances for orthodontic treatment, may be comprised of at least one space filler shaped to align with a gap between adjacent teeth. If a tooth is extracted from a patient's dentition, a space or gap will be left behind between adjacent teeth. A similar gap may also be present due to general misalignment of the teeth. An elastic positioning appliance may be made to be positioned over a gap and its surrounding teeth. In such a case, a space filler may be shaped to align with the gap. In a preferred embodiment, the space filler may be a cavity in the polymer shell having the shape of at least a portion of a tooth, dental feature, sphere, oval or three-dimensional curved and/or flat sided object. In the case of a tooth shape, the space filler may act as a "pontic," a fake tooth placed where a tooth is missing to give the appearance of the presence of a tooth. This same effect may also be given by other shapes. Likewise, as a gap is gradually eliminated due to repositioning of the teeth, a variety of shapes may be suitable throughout the repositioning process.

To further conceal the presence of a space or gap between teeth during orthodontic treatment, a space filler may be opacified. By making the space filler at least partially opaque, it may give a more convincing appearance of the presence of a tooth or dental feature. Such opacity may be an effect of surface treatment of the space filler. For example, the inside and/or outside surfaces of the space filler may be painted with a tooth-colored material. Alternatively, the surfaces may be microetched to give a more frosted appearance to the polymeric shell material. In either case, the space or gap may be less visible.

In addition to improving cosmetic appearance, a space filler may also provide structural support for the elastic appliance. When a space filler is a cavity, as described above, the presence of the cavity improves the structural integrity of the appliance by providing a uniform geometry. Alternatively, a space filler may be any number of structures providing similar support. For example, a space filler may be a structure that is at least partially solid. This may be achieved by the formation of a solid section of material spanning the gap, similar to a bridge or slab between adjacent teeth. Such a solid section may be formed by the fusing of the walls of the polymeric shell together. Alternatively, the shell may be filled with a solid material. In this case, the shell may be designed with undercuts or prongs to retain the solid material. In addition, a solid section may be corrugated to additionally improve the integrity of the appliance.

In a fourth aspect of the present invention, a removable dental positioning appliance, typically used in a series of successive elastic appliances for orthodontic treatment, may be comprised of a polymeric shell having cavities shaped to receive and reposition teeth, wherein one or more cavities has a window to expose at least a portion of a received tooth. Such windows may be portions of the wall of the polymer shell which are removed. When the shell is positioned over the patient's teeth, portions of the teeth beneath the windows may be exposed. Exposing such tooth surfaces may allow brackets, buttons or other orthodontic components to be utilized in conjunction with the elastic appliance or to be exposed for other purposes.

In a preferred embodiment, a polymeric shell may have a plurality of windows over portions of the occlusal surfaces of the teeth. In this case, segments of the shell may still be present along the facial and lingual surfaces of the teeth and across the interdental regions or spaces between the teeth. Exposure of the occlusal surfaces in appropriate size and location may allow interdigitation of the upper and lower teeth. This may also be achieved with the presence of one or a few larger windows over portions of the occlusal surfaces of the teeth. In these cases, segments of the shell may not be present across the interdental regions or spaces between the teeth. In either case, interdigitation of at least portions of the upper and lower teeth may benefit tooth and jaw orientations, leading to improved treatment, appearance, comfort and consequently patient compliance. Likewise, similarly placed windows may provide the benefits offered by a lower elastic modulus, such that the lowest stiffness may be provided by the absence of the material. Such benefits and a full description is provided in co-pending application Ser. No. 09/616,830, assigned to the assignee of the present invention.

DESCRIPTION OF THE SPECIFIC EMBODIMENTS

Traditional orthodontic treatment often involves the use of basic repositioning devices, such as braces, and the use of supplementary devices, components or accessories to achieve desired end results. As previously described, such supplementary components may be mounted on fixed, non-removable devices or they may be part of a removable appliance typically worn prior to the application of the fixed devices. As with traditional treatment, it may be desired to utilize similar supplementary components when repositioning teeth with removable elastic repositioning appliances. Due to the nature of elastic appliances, such components may take a variety of forms ranging from readily available traditional accessories to specially created devices, as will be described below.

Figure 1:
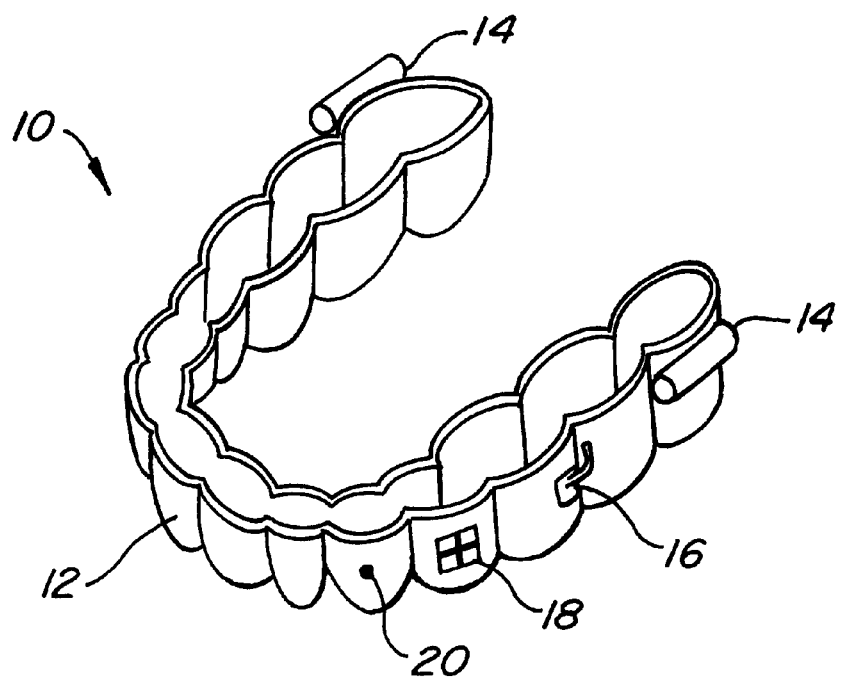
FIG. 1 is a perspective illustration a variety of orthodontic components or accessories typically used with fixed orthodontic devices mounted on or embedded in the polymeric shell of a removable elastic repositioning appliance.

Referring to FIG. 1, a variety of orthodontic components or accessories typically used with fixed orthodontic devices, such as braces, are shown in conjunction with a removable elastic positioning appliance 10. The majority of these accessories may be readily available since they are typically used with conventional treatment. They are also typically mounted on fixed devices, so they are available as separate individual components. As previously described, these components may be embedded in the polymeric shell 12 of an elastic repositioning appliance 10 during production or they may be mounted on the shell 12 in a post-production assembly. One such type of component is a tube 14 which is used in pairs to mount a headgear appliance. Headgear appliances are typically mounted on opposite posterior molars of the upper jaw for a number of purposes, including keeping the upper jaw from growing, pulling the upper teeth backward, and pulling the upper jaw and teeth upward and backward so that they align with the lower jaw and teeth. Therefore, tubes 14 for receiving headgear may be mounted on the buccal surfaces of the polymeric shell 12 covering the posterior molars. The distal ends of the headgear which enter the oral cavity may then be inserted into the tubes 14 to apply extra oral forces to the teeth and jaw. Other components may include hooks 16, primarily used for mounting elastic bands, brackets 18, used for mounting additional components and accessories or possibly for interconnection with fixed brackets or devices, and buttons 20, primarily used as an attachment point for various purposes. It may be appreciated that such components have been shown on the same appliance 10 for illustrative purposes, however typical use may involve one or a few of such components with varying arrangements.

Figure 2:
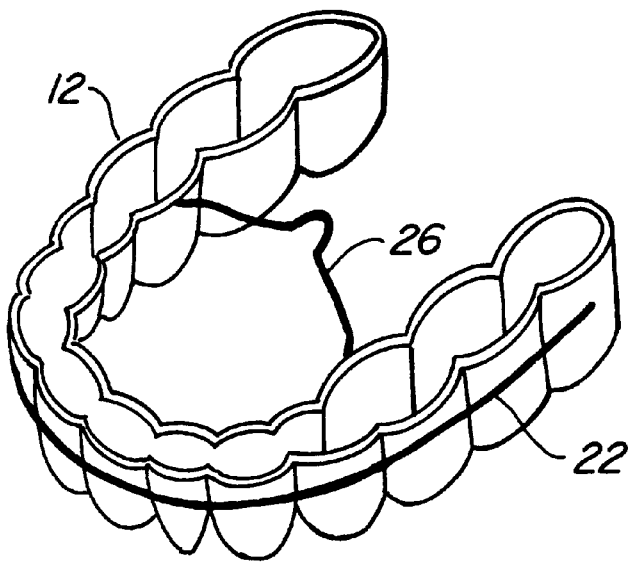
FIG. 2 is a perspective illustration of a typical transpalatal arch bar mounted on or embedded in the polymeric shell of an appliance.

Referring to FIG. 2, an additional component which may be mounted on or embedded in a polymeric shell 12 is a transpalatal arch bar 26. Such palatal bars typically span the palate and are fixed at both ends to permanent devices mounted on opposing molars. This is often used to stabilize and maintain positioning after active arch expansion. In the case of an elastic repositioning appliance 10, the conventional arch bar 26 may be positioned in a similar location, attached at both ends to the polymeric shell covering the lingual surfaces of opposing upper molars. In addition, a low hanging transpalatal bar for control of vertical dimension may be used. Also shown in FIG. 2, one or more wires 22 may be mounted on or embedded in the polymeric shell 12. Such wires 22 may span the majority of the arch, as in the case of a conventional archwire, as shown. Or, such wires 22 may span only portions of the arch, may be present on or within the facial and/or lingual surfaces of the shell, may be multiple in number at a given location, and may be curved, straight or a combination of these, to name a few. The presence of such a wire 22 may be used most commonly for structural reinforcement but may also be used to aid in the application of orthodontic repositioning forces. Again, it may be appreciated that such components have been shown on the same appliance 10 for illustrative purposes, however typical use may involve one or a few of such components with varying arrangements.

Figure 3:
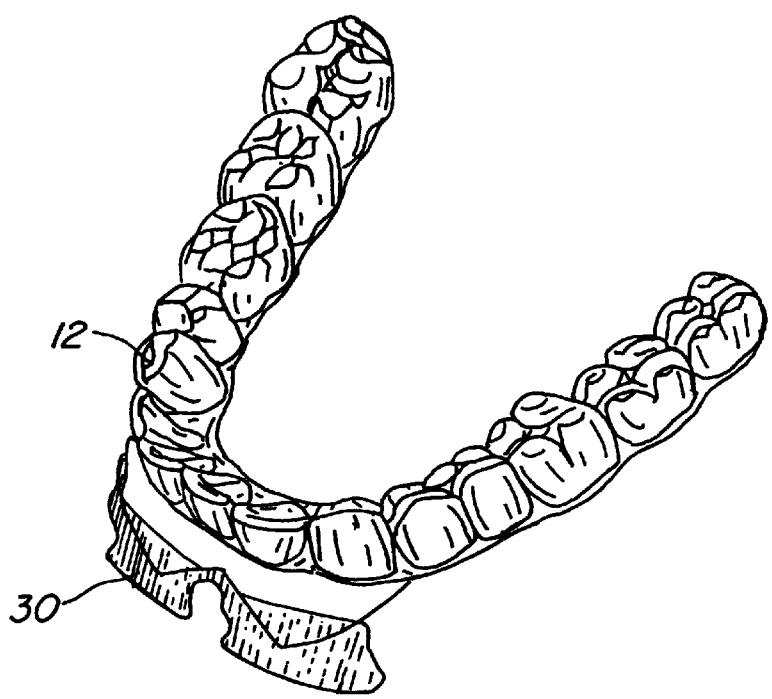
FIG. 3 is a perspective illustration an appliance having a lip pad.

FIGS. 3–8 illustrate the use of a variety of orthodontic components or accessories which are typically used with removable functional appliances. These components are not generally suited for use with fixed appliances and devices due to their bulk and size. However, they may be readily used with removable elastic repositioning appliances. In most functional appliances, flanges are used to provide the stimulus to posture the mandible to a new position. Growth modification is most effective if the patient uses his or her own musculature to posture the mandible forward, as opposed to the mandible being held forward by external pressure while the patient relaxes. Thus, the key to mandibular repositioning is the contact of the pad or flange with soft tissue. Such pads or flanges may be mounted or embedded in elastic repositioning appliances. Referring to FIG. 3, a lip pad 30 may be positioned on the polymeric shell 12 so that it is low in the vestibule, holding the lips away from the teeth and forcing the lips to stretch to form an oral seal. This forces the lip musculature to stretch during function, presumably improving the tonicity of the lips and perhaps promoting some soft tissue remodeling that would contribute to stability of changes in incisor position.

Figure 4:
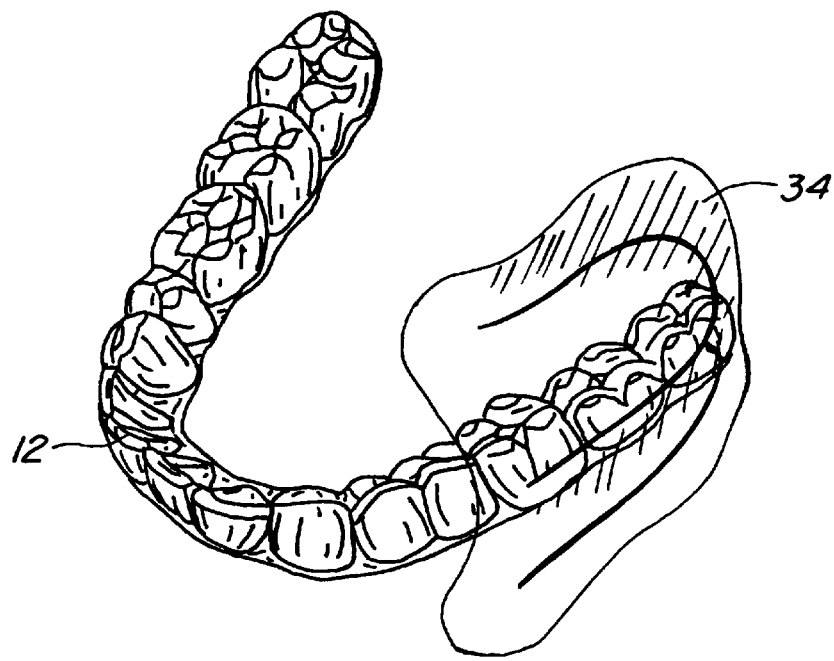
FIG. 4 is a perspective illustration of an appliance having a buccal shield.
Figure 5:
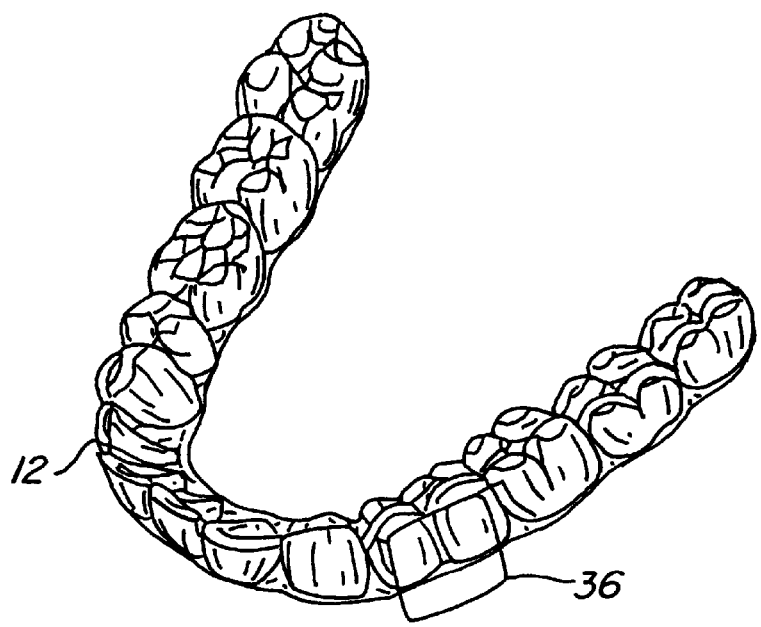
FIG. 5 is a perspective illustration of an appliance having buccinator bow.
Figure 6:
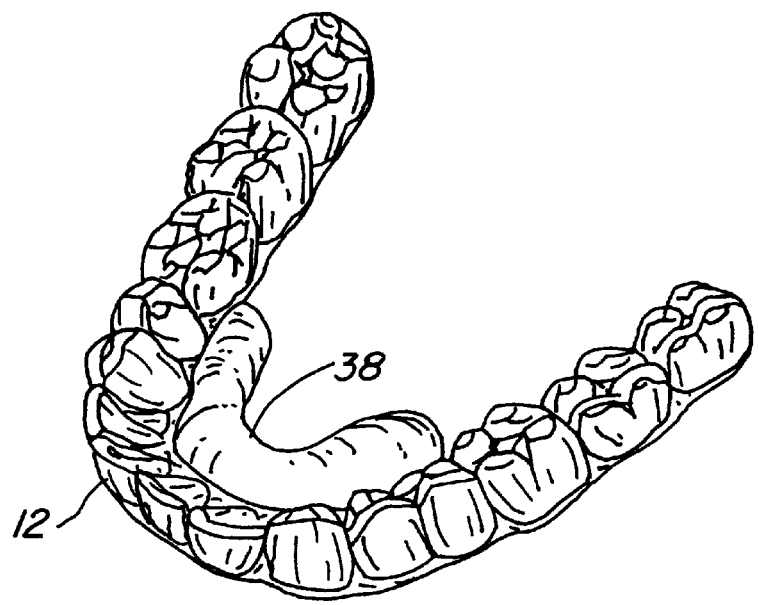
FIG. 6 is a perspective illustration of an appliance having lingual pad.

Referring to FIGS. 4 and 5, plastic buccal shields 34 and wire buccinator bows 36 may be mounted on or embedded in the polymer shell 12 to hold the soft tissues away from the teeth. A buccal shield 34 or bow 36 may be positioned on the buccal surface of the polymeric shell 12 to lie between the teeth and the cheek. The buccal shield 34 is most useful to hold the cheek away from the dentition to facilitate posterior dental expansion by disrupting the tongue-cheek equilibrium. This in turn leads to facial movement of the teeth and arch expansion. A combination of lip pads 30 and buccal shields 34 will result in an increase in arch circumference as well. It may be appreciated that similar shields may be mounted on the lingual surface of the polymeric shell to remove the resting tongue from between the teeth. This has the effect of enhancing tooth eruption in designated areas. In addition, a lingual pad or flange 38 may be positioned on the lingual surfaces of the polymeric shell 12 covering the lower anterior teeth, as shown in FIG. 6. The lingual pad 38 determines the anteroposterior and vertical mandibular posture for most functional appliances. Such pads 38 may not only position the mandible forward but also exert a protrusive effect on the mandibular incisors when the mandible attempts to return to its original position.

Figure 7:
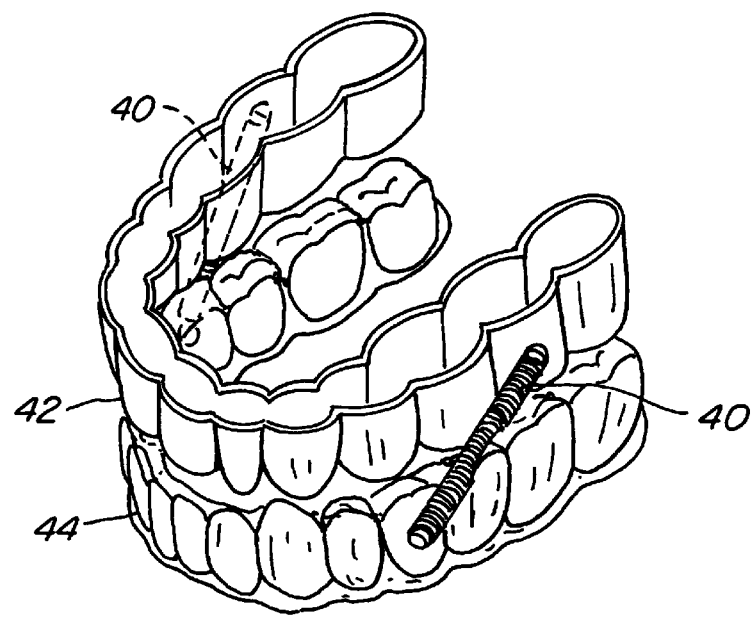
FIG. 7 is a perspective illustration of appliances joined by frameworks used in Herbst Appliances.
Figure 8:
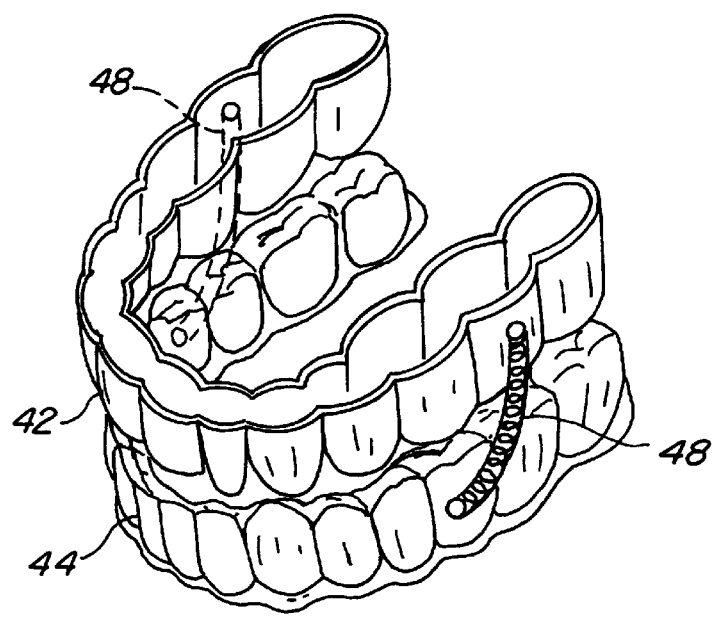
FIG. 8 is a perspective illustration of appliances joined by frameworks used in Jasper Jumpers.

Referring to FIGS. 7 and 8, a number of components and accessories may be removably or fixedly attached to both an upper and lower elastic positioning appliance. Components commonly used in this arrangement are frameworks used in Herbst Appliances and Jasper Jumpers. Herbst Appliances are devices in which the maxillary and mandibular arches are splinted with frameworks that are connected with a pin-and-tube device that holds the mandible forward. When used with elastic repositioning appliances, FIG. 7, the pin-and-tube apparatus 40 may be mounted on the buccal surfaces of the upper polymeric shell 42 and lower polymeric shell 44 as shown. The Jasper Jumper functions in a similar manner as the maxillary and mandibular arches are splinted with frameworks that are connected with a spring covered by a plastic sheath. When used with elastic repositioning appliances, FIG. 8, the sheath covered spring 48 may be mounted in a similar manner as shown.

Figure 9:
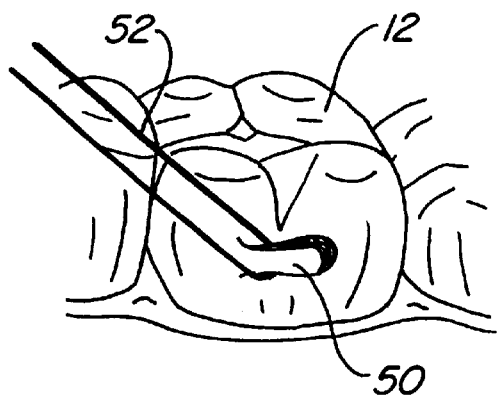
FIG. 9 illustrates of an appliance having a protrusion formed in the polymeric shell in the shape of a hook.
Figure 10A:
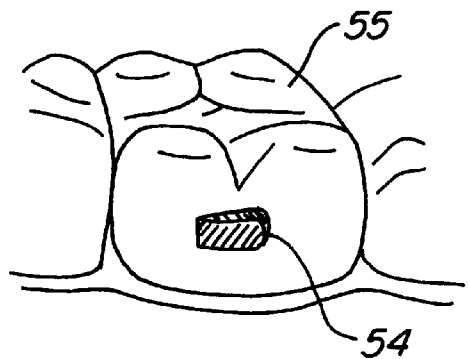
FIGS. 10A and 10B illustrate steps of producing a protrusion depicted in FIG. 9.
Figure 10B:
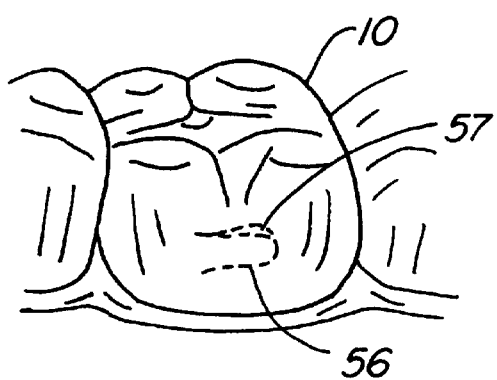

As an alternative to mounting or embedding conventional orthodontic components on an elastic repositioning device, protrusions or other shapes may be formed in the polymeric shell of the device to be used for orthodontic functions. For example, referring to FIG. 9, a hook 50 may be formed in the polymeric shell 12 of an elastic repositioning appliance 10 for use in mounting a flexible band 52. Such a hook 50 may resemble traditional hooks found in dental care, or it may be specially designed for use with elastic repositioning appliances. The embodiment illustrated in FIG. 9 may be produced by a series of production steps. First, a mold of the dentition is produced by any method. Second, FIG. 10A, a wedge or similar protruding mass 54 is then mounted on the mold 55 in the location desired for the resulting hook. It may be appreciated that such a protruding mass 54 may be formed in the original mold 55 by a variety of methods, particularly in the case of computer-guided production methods. Next, a polymeric sheet is thermoformed over the mold 55 to form the appliance 10. The appliance 10 may then be trimmed along the dashed line 56, FIG. 10B, and the polymeric material removed from the joining area 57 to create a hook 50 shown in FIG. 9.

Figure 11:
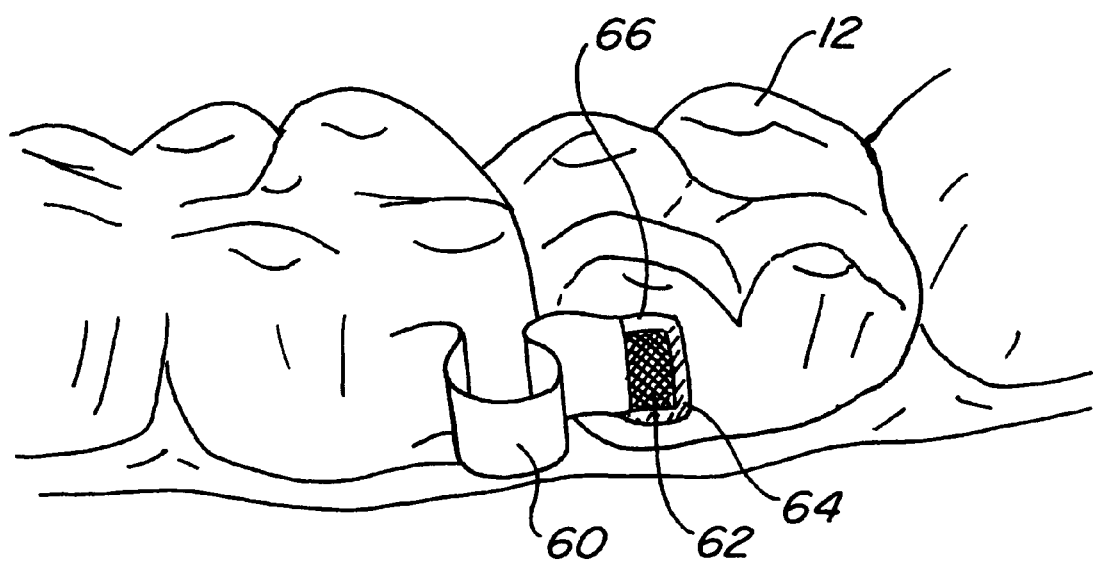
FIG. 11 illustrates an appliance having a protrusion formed in the polymeric shell in the shape of a spring.

In another embodiment, shown in FIG. 11, a spring 60 may be formed in the polymeric shell 12 of an elastic repositioning appliance 10 for use in transmitting repositioning force to one or more teeth. Such a spring 60 may resemble traditional springs found in dental care, or it may be specially designed for use with elastic repositioning appliances. In this example, the spring 60 is comprised of a pre-formed strip or portion of the polymeric shell 12 which engages an attachment body 62 mounted on an underlying tooth 64. The attachment body 62 is accessible through a window 66 in the appliance 10.

Figure 12:
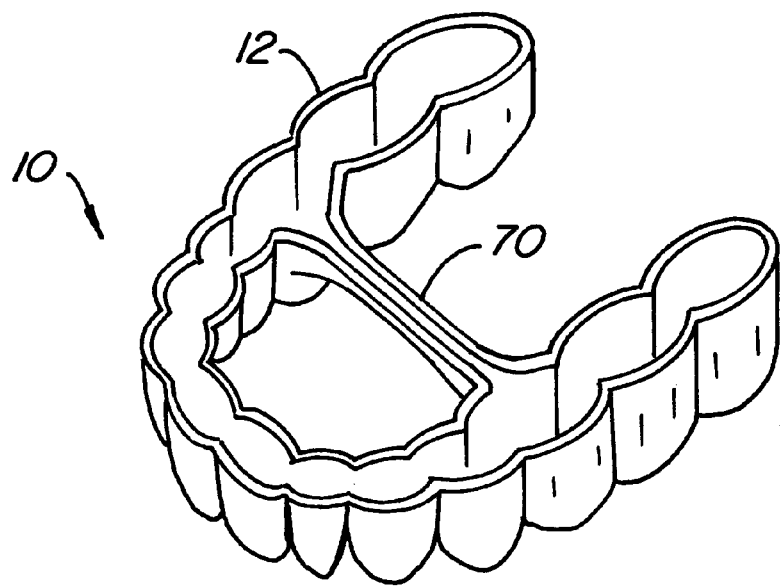
FIG. 12 is a perspective illustration of an appliance having a protrusion in the polymeric shell to form a transpalatal bar.
Figure 13:
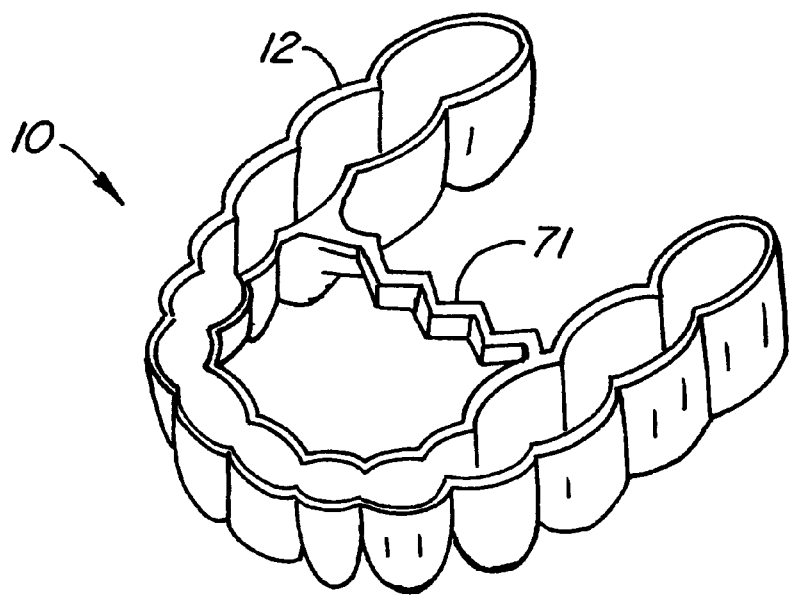
FIG. 13 is a perspective illustration of an appliance having a corrugated protrusion in the polymeric shell to form a transpalatal bar.

In further embodiments, larger protrusions may also be formed in the polymeric shell to provide additional support for the appliance and/or to provide orthodontic functions. Such a protrusion may form a palatal bar 70, as shown in FIG. 12. Here, a palatal bar 70 is formed in the polymeric shell 12 itself. In addition, a variety of palatal bars may be formed in the shell, such as a low hanging transpalatal bar for control of vertical dimension. These may provide orthodontic functions as described above in relation to conventional palatal bars, and they may also provide support for the appliance 10. This may be particularly useful in highly flexible appliances. For increased support of the construction, the protrusion may be a corrugated palatal bar 71, as shown in FIG. 13.

Figures 14A, 14B:
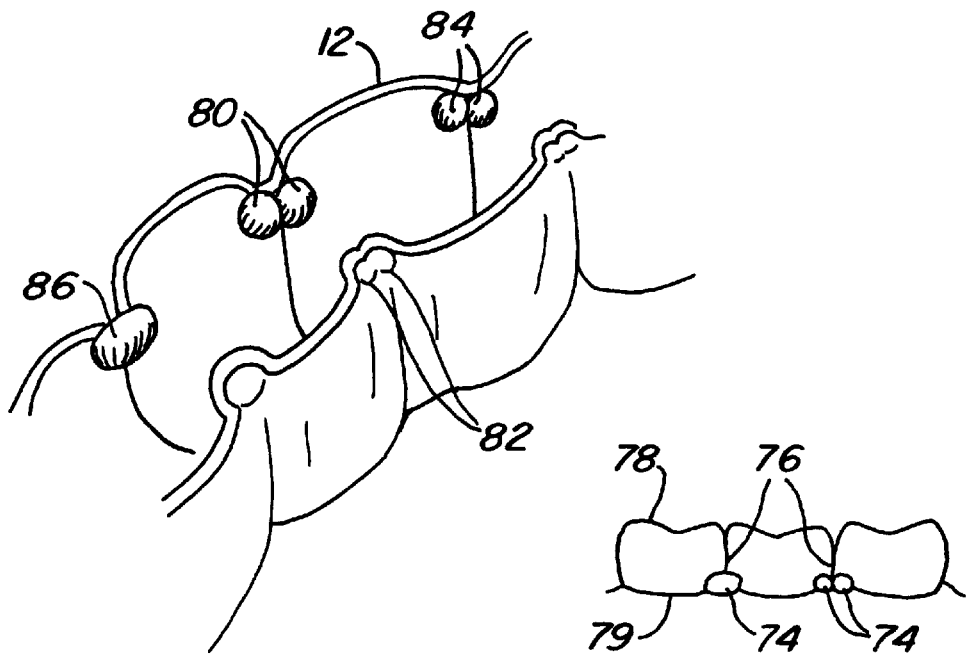
FIG. 14A is a side view of a patient's teeth showing the placement of protruding divots contacting interdental areas.
FIG. 14B is a perspective illustration of a portion of an appliance having such divots.

In still further embodiments, protrusions in an elastic repositioning appliance may assist in holding the elastic appliance in place when it is properly inserted and positioned. Such protrusions may be divots 74 sized and located to contact interdental areas 76 of the patient's teeth 78, often near the gingival margin 79 as shown in FIG. 14A. Such placement may provide additional friction and "grab" in dental regions conducive to this effect. Such divots 74 may be most visible by viewing the hollow cavities of the appliance 10, as shown in FIG. 14B. These protrusions may be solid divots 80 adhered to or embedded in the polymeric shell 12 to inwardly protrude from the wall. Alternatively, the protrusions may be formed divots 82 in the wall of the polymeric shell 12 so that essentially the wall protrudes inwardly in these areas. As shown, the divots may be of any shape, number and configuration, including paired divots 84 and single divots 86 as shown.

Figures 15A, 15B:
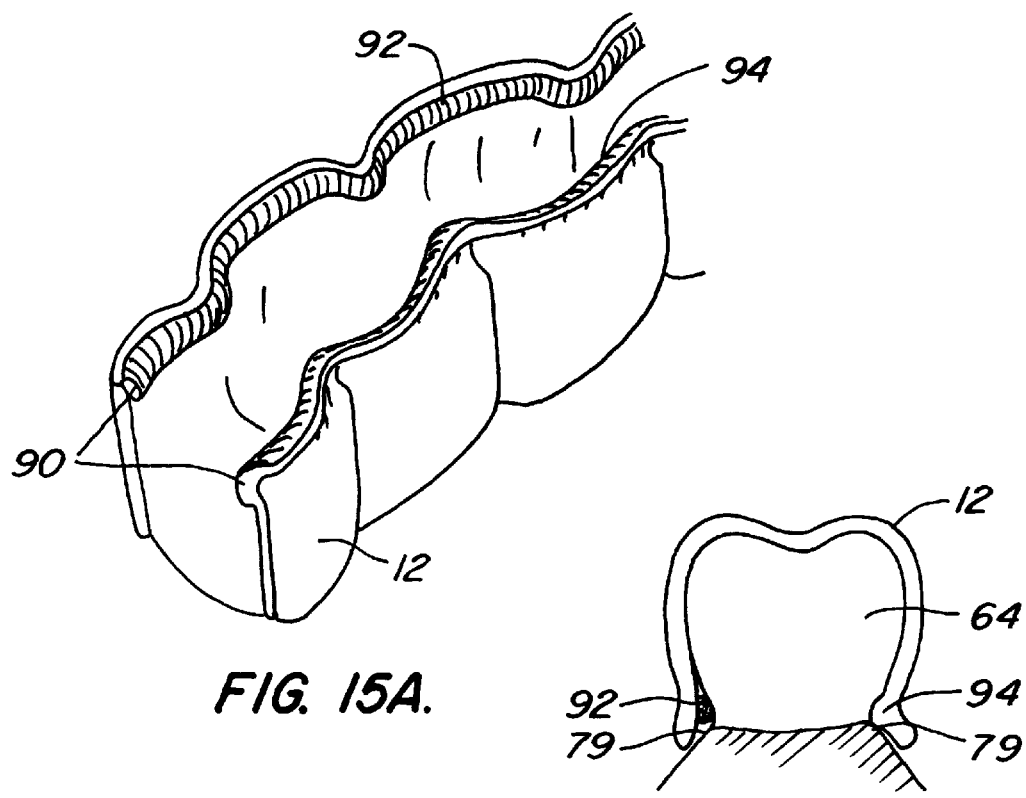
FIG. 15A is a perspective illustration of a portion of an appliance having a continuous protrusion along the gingival line.
FIG. 15B is a cross-sectional view of a tooth having such an appliance in place.

Similarly, these protrusions may be a continuous protrusion contacting more than one tooth along the gingival margin and the interdental areas. This is illustrated in FIG. 15A as a continuous protrusion 90 is shown along the edges of the hollow cavities of the appliance. This may be a solid protrusion 92 adhered to or embedded in the polymeric shell 12 to inwardly protrude from the wall, or it may be a formed protrusion 94 in the wall of the polymeric shell 12 so that essentially the wall protrudes inwardly in these areas. When the appliance is positioned over the teeth, such a protrusion 90 may fit in the undercut of the tooth 64 along the gingival margin 79, as shown in FIG. 15B. Here a solid protrusion 92 and a formed protrusion 94 are shown in cross-section. Such positioning along the undercut of the teeth may assist in holding the appliance in place. It may be appreciated that such a protrusions may be sized, formed and located in any combination within the polymer shell so as to assist in holding the appliance in a desired position.

Figure 16:
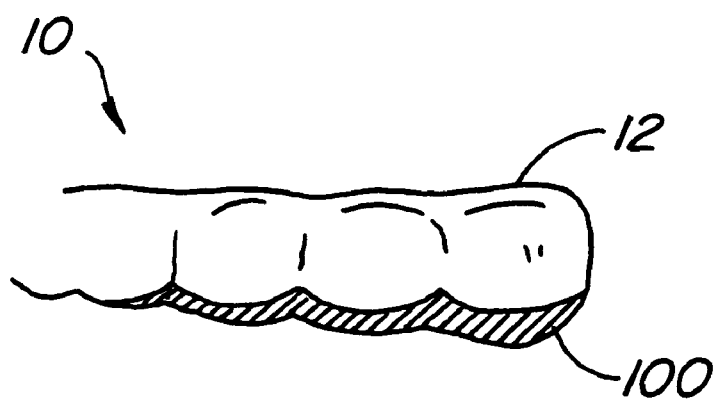
FIG. 16 is a side view of a posterior portion of an appliance illustrating an increase in thickness of material to form a bite plate.
Figure 17:
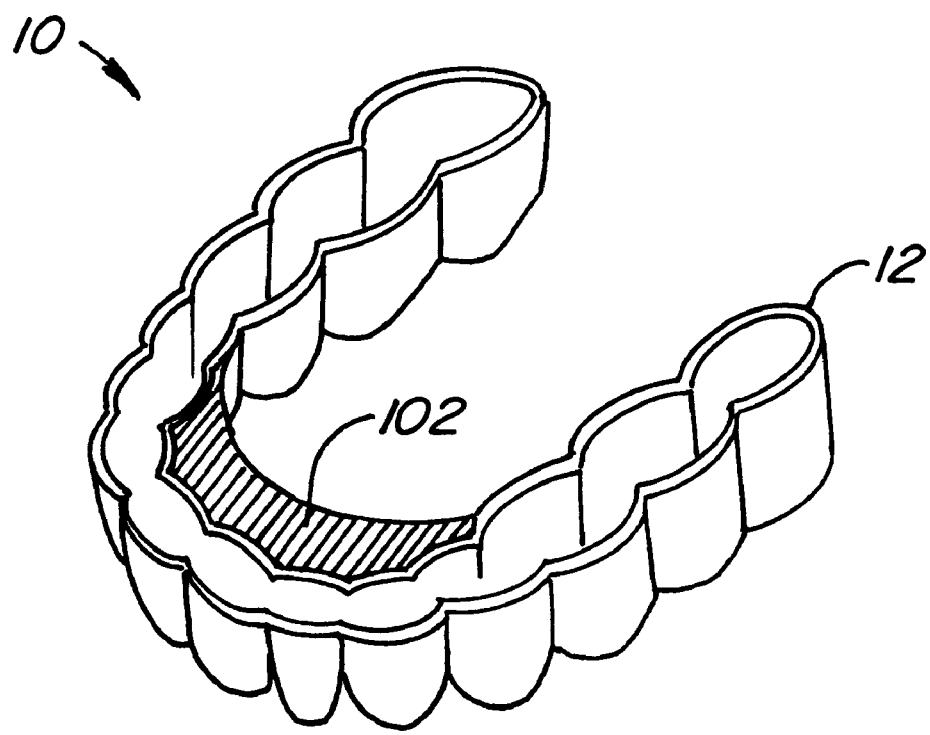
FIG. 17 is a perspective illustration of an appliance having a protrusion of an upper palatal region to form a bite plate.

In another embodiment, the one or more protrusions may form a bite plate. A bite plate is a device which prevents the teeth from closing completely. The resulting open state, or disclusion, may be useful for a number of orthodontic treatments, including crossbite correction and controlled passive eruption. To provide anterior disclusion, an elastic positioning appliance 10 may have an increase in thickness of material 100 in the posterior occlusion regions of the polymeric shell 12, as shown in FIG. 16. The increase in thickness of material 100 may be applied to the appliance 10 or formed by the appliance 10 to create a protrusion over the designated occluding surfaces. Similarly, as shown in FIG. 17, posterior disclusions may be provided by forming a protrusion 102 in the polymer shell 12 which extends at least a portion of an upper palatal region with added thickness. This protrusion may be formed in the appliance 10 or applied to the surface of the appliance 10.

Figure 18A:
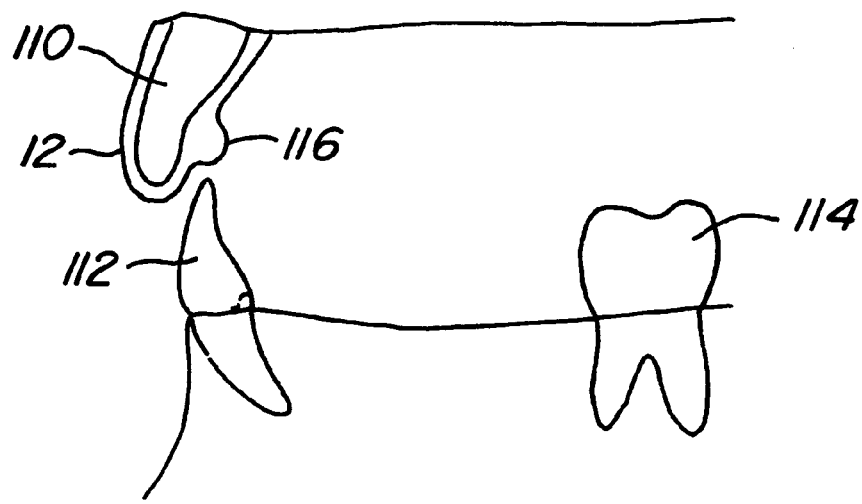
FIGS. 18A and 18B are cross-sectional views of appliances having protrusions in an upper lingual and lower facial anterior regions, respectively, to form bite plates.
Figure 18B:
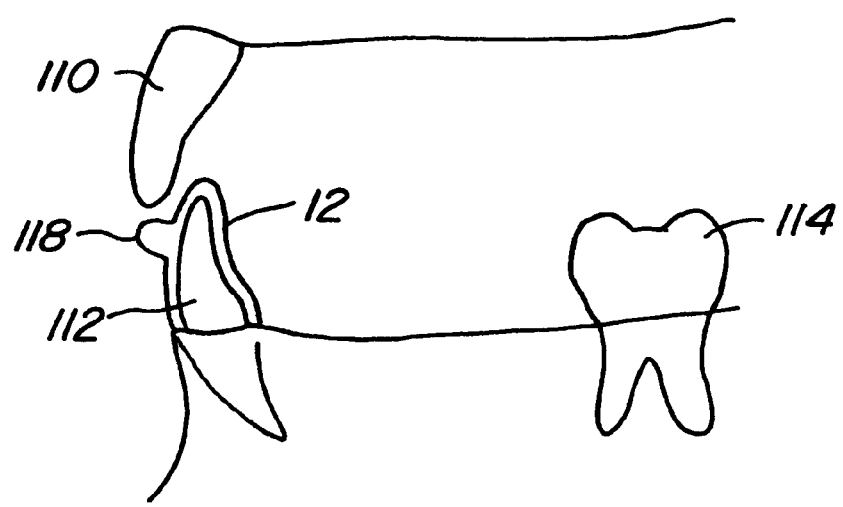

Alternatively, posterior disclusions may be provided by forming a protrusion in an upper lingual or lower facial anterior region, as depicted in FIGS. 18A and 18B. Here, the bite is shown in cross-section, with an upper incisor 110 overlapping a lower incisor 112 and a molar 114 positioned for reference. In FIG. 18A, the polymeric shell 12 of an elastic positioning appliance 10 is shown covering the upper incisor 110. On the lingual surface of the shell 12, a protrusion 116 is shown which may contact the lower incisor 112 during biting, thus acting like a bite plate. This protrusion 116 may be formed into the polymeric shell 12 or applied along the lingual surfaces of the appliance 10. Such an arrangement may thus provide posterior disclusions. Similarly, the polymeric shell 12 may cover the lower incisor 112, as shown in FIG. 18B. In this case, a protrusion 118 on the facial surface of the shell 12 is shown which may contact the upper incisor 110 during biting. Again, this protrusion 118 may be formed into the polymeric shell 12 or applied along the facial surfaces of the appliance 10. This arrangement may also provide posterior disclusions.

Figure 19:
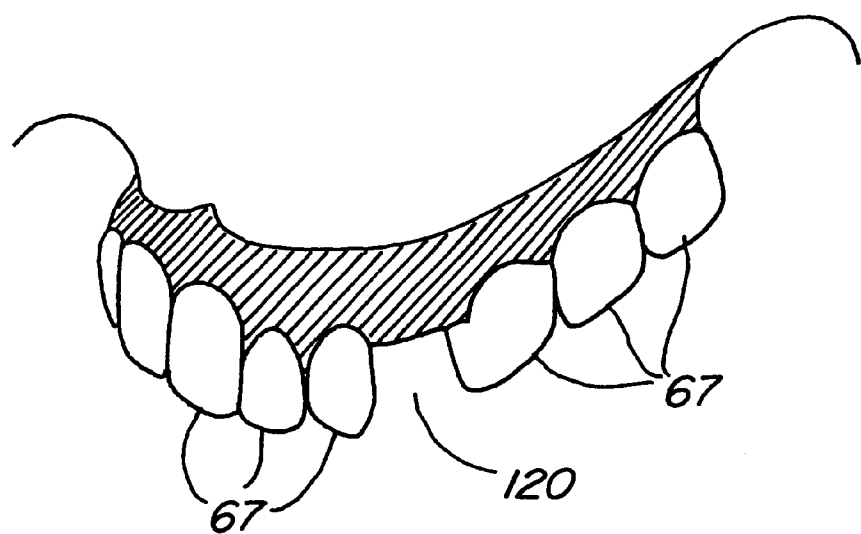
FIG. 19 illustrates a patient having a gap between adjacent teeth.
Figure 20:
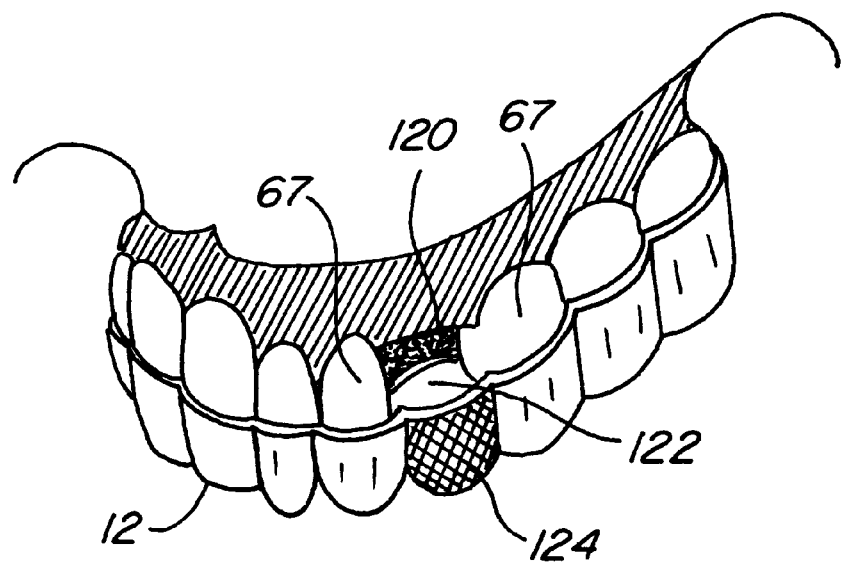
FIG. 20 is a perspective illustration of an appliance having a space filler cavity in the shape of a tooth placed over the patient's dentition illustrated in FIG. 19.

Referring to FIG. 19, many patient's dentition present a gap 120 or space between adjacent teeth 67. Such a gap 120 may be the size of a tooth 67, as may be the case when a tooth is extracted, or the gap 120 may be larger or smaller than the size of a typical tooth 67, as is often the case due to general misalignment of the teeth. In either case, an elastic positioning appliance 10 may be made to be positioned over the gap 120 and the surrounding teeth 67 with a space filler aligning with the gap 120. In a preferred embodiment, shown in FIG. 20, the space filler may be a cavity 122 in the polymer shell 12 having the shape of a tooth. Thus, the space filler may act as a "pontic", a fake tooth placed where a tooth is missing to give the appearance of the presence of a tooth. Likewise, such a cavity 122 may have the shape of any portion of a tooth, dental feature, sphere, oval or three-dimensional curved and/or flat sided object for any desired effect. To further conceal the presence of a space or gap 120 between teeth 67 during orthodontic treatment, the space filler may be opacified, as depicted by shading 124 in FIG. 20.

Figure 21:
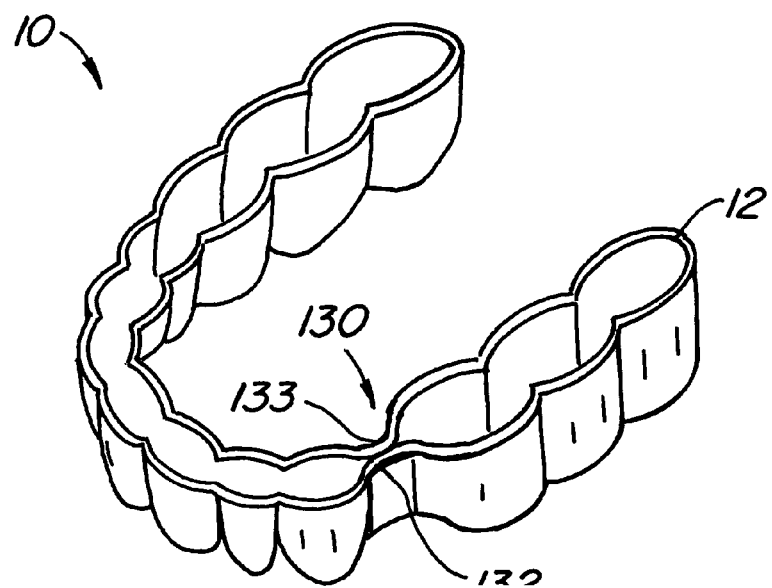
FIG. 21 is a perspective illustration of an appliance having a space filling structure formed between two cavities in the polymeric shell.
Figure 22:
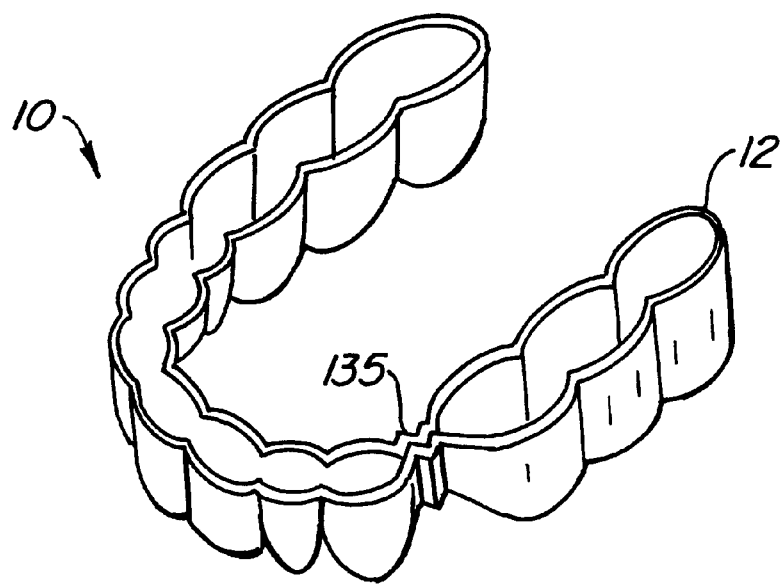
FIG. 22 is a perspective illustration of an appliance having a space filling corrugated structure formed between two cavities in the polymeric shell.

In addition to improving cosmetic appearance, a space filler may also provide structural support for the elastic appliance. When a space filler is a cavity, as described above, the presence of the cavity improves the structural integrity of the appliance by providing a uniform geometry. Alternatively, a space filler may be any number of structures providing similar support. In a preferred embodiment, shown in FIG. 21, the space filler may be a structure 130 formed between two cavities in the polymeric shell 12 of an appliance 10. The structure 130 may be comprised of the facial wall 132 and lingual wall 133 of the polymeric shell 12 fusing together to form an at least partially solid slab or bridge. In addition, suitable fillers or reinforcements may be used in the fusing or similar process for added support. Likewise, a corrugated structure 135 may be formed between the cavities, as shown in FIG. 22. Such corrugation may further reinforce the structure for added support. In any case, a designated cavity 122 or structure 130, 135 in the polymeric shell 12 may be designed to align with a gap 120 between adjacent teeth 67 when the appliance 10 positioned over the patient's teeth for improved cosmetic appearance and/or structural support.

Figure 23A:
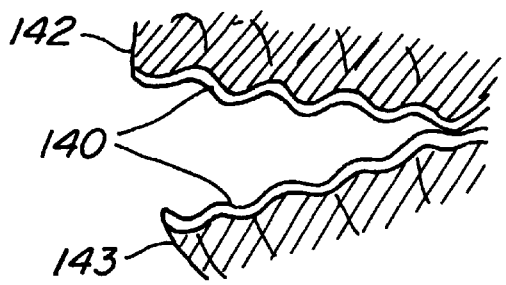
FIG. 23A illustrates an unwanted disclusion due to thickness of the appliance along the occlusional surfaces.
Figure 23B:
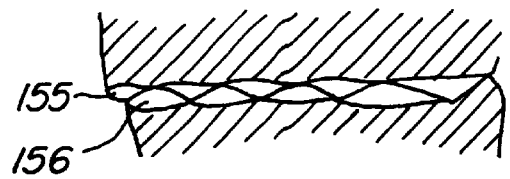
FIG. 23B illustrates the elimination of the disclusion of FIG. 23A by eliminating material along the occlusional surfaces.
Figure 23C:
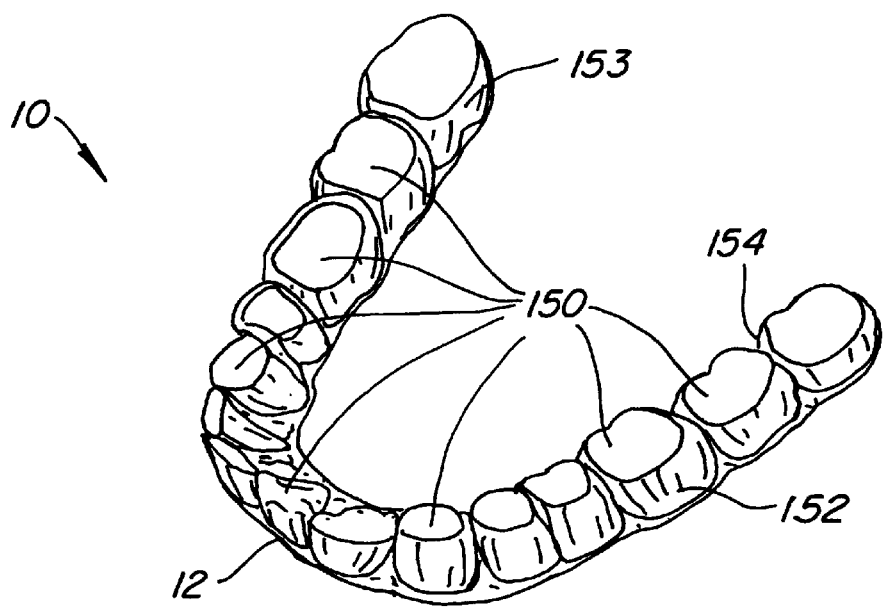
FIG. 23C illustrates a preferred embodiment of an appliance with portions of the occlusional surfaces eliminated.

Although forming protrusions or adding additional material to elastic repositioning appliances may provide useful features in orthodontic treatment, it may also be beneficial to remove material or form windows in an appliance. Referring to FIG. 23A, if the occlusional surfaces 140 of an upper appliance 142 and a lower appliance 143 are relatively thick, simultaneous wearing of the appliances 142, 143 may provide unwanted disclusion of the teeth. For example, when closing the jaws, the double layer of occlusional surfaces 140 between the jaws may cause the posterior teeth to prematurely contact, thus preventing the anterior teeth to suitably close. This may be avoided by reducing or eliminating the occlusional surfaces of the appliances, as shown in FIGS. 23B and 23C. In a preferred embodiment, shown in FIG. 23C, a polymeric shell 12 of an appliance 10 may have a plurality of windows 150 in the portions which cover the occlusal surfaces of the teeth. In this example, segments of the shell 12 are still present along the facial surfaces 152 and lingual surfaces 153 of the appliance 10 and across the interdental regions 154 or spaces between the teeth. When such an appliance is placed over the upper teeth 155 and lower teeth 156, the teeth may interdigitate, as shown in FIG. 23B. Interdigitation of at least portions of the upper and lower teeth may benefit tooth and jaw orientations, leading to improved treatment, appearance, comfort and consequently patient compliance.

Figure 24A:
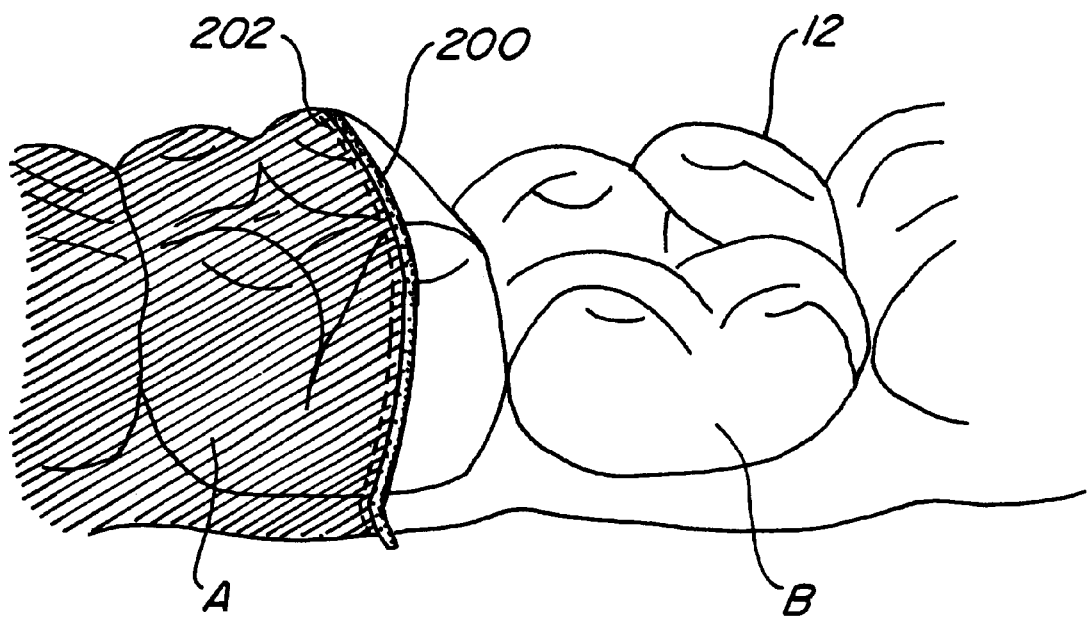
FIG. 24A illustrates a release tab embedded in the polymeric shell of an appliance.
Figure 24B:
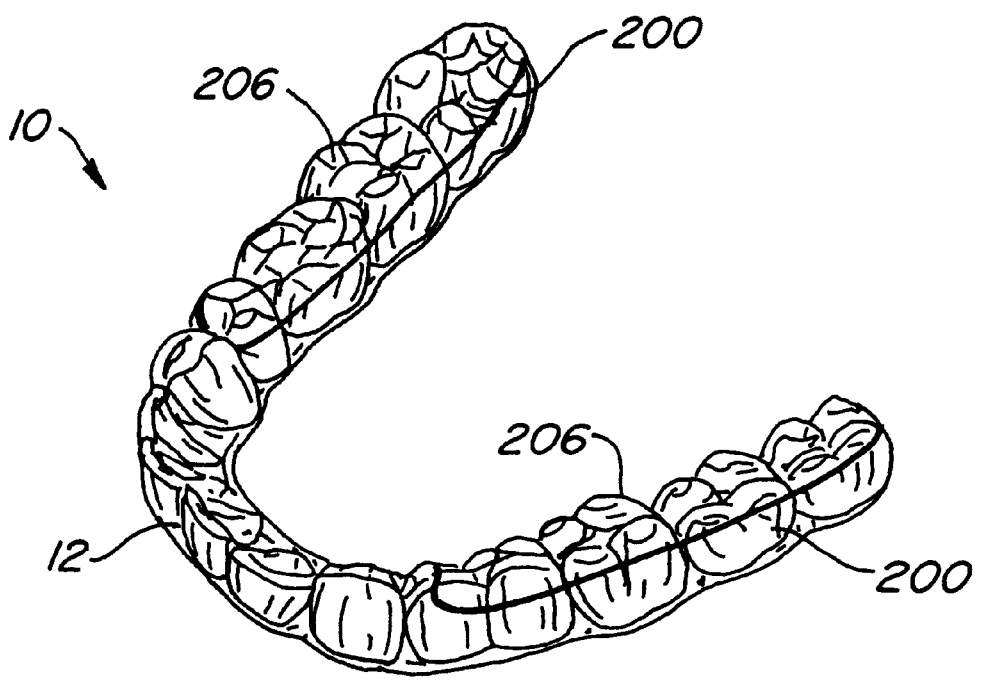
FIG. 24B illustrates a preferred embodiment of an appliance with release tabs encircling areas of occlusional surfaces of the appliance.

Removal of material may be aided by the use of a release tab 200, as shown in FIGS. 24A and 24B. A release tab 200 may be used to remove a layer of material from the polymeric shell 12 or to remove an entire portion of the shell 12, such as to either create a window, as described above, or to eliminate the shell 12 from covering specific teeth or portions of the patient's teeth. Referring to FIG. 24A, a release tab 200 may be embedded in the polymeric shell 12 along a line 202 for future separation between portion A (shaded) and portion B. Although such a line 202 is depicted as a dashed line adjacent to the tab 200 edge, such a line 202 may lie directly over the tab or in any close relation to the tab 202. In the case of a polymeric shell 12 comprised of multiple layers of material, the tab 200 may be embedded between the layers with a portion exposed for grasping. By grasping the tab 200 and pulling the tab 200 along its length, one or more layers of material may be released along a line 202 of separation and removed from the shell 12. In this example, the result may be portion A comprising two layers of material and portion B comprising only one. Alternatively, the result may be portion A comprising one or more layers and portion B removed entirely. Other combinations or examples are possible. Such alterations may be beneficial for patient comfort, ease of use, or obtainment of orthodontic repositioning goals, to name a few. FIG. 24B illustrates a preferred embodiment of placement of such a release tab 200 in a polymeric shell 12 of an elastic repositioning appliance 10. The tab 200 may be placed to encircle areas 206 of the occlusional surfaces of the appliance 10. Thus, the orthodontic treatment of a patient may allow material in these areas 206 of an appliance 10 for a given duration of the treatment plan. At a given point in the treatment, the orthodontic practitioner may prefer to remove a layer of material or the material entirely in these areas 206 during a patient office visit. The practitioner may perform such a removal by pulling on the appropriate release tabs 200 as described above. This may thus reduce time and cost of patient treatment.

Although the forgoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A removable dental positioning appliance comprising: a polymeric shell having cavities shaped to receive and reposition teeth from a first orientation to a successive orientation and at least one space filler shaped to align with a gap between adjacent teeth, wherein the at least one space filler is a corrugated structure between adjacent teeth.

\* \* \* \* \*